(12) United States Patent
Fujimori et al.

(10) Patent No.: US 10,865,425 B2
(45) Date of Patent: Dec. 15, 2020

(54) SYSTEM FOR PRODUCING ORGANIC SUBSTANCE AND METHOD FOR PRODUCING ORGANIC SUBSTANCE

(71) Applicant: SEKISUI CHEMICAL CO., LTD., Osaka (JP)

(72) Inventors: Yoji Fujimori, Ibaraki (JP); Kazumi Okada, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 26 days.

(21) Appl. No.: 16/307,674

(22) PCT Filed: Sep. 16, 2016

(86) PCT No.: PCT/JP2016/077516
§ 371 (c)(1),
(2) Date: Dec. 6, 2018

(87) PCT Pub. No.: WO2017/212662
PCT Pub. Date: Dec. 14, 2017

(65) Prior Publication Data
US 2019/0256874 A1    Aug. 22, 2019

(30) Foreign Application Priority Data

Jun. 9, 2016    (WO) .................. PCT/JP2016/067225

(51) Int. Cl.
*B01D 53/04*    (2006.01)
*C10K 1/28*    (2006.01)
(Continued)

(52) U.S. Cl.
CPC ................ *C12P 7/065* (2013.01); *C01B 3/02* (2013.01); *C01B 3/56* (2013.01); *C10K 1/28* (2013.01);
(Continued)

(58) Field of Classification Search
CPC .. B01D 53/04; B01D 53/047; B01D 53/0462; C01B 3/02; C01B 3/56; C01B 2203/042;
(Continued)

(56) References Cited

U.S. PATENT DOCUMENTS 8,211,679 B2    7/2012  Datta et al.
8,752,390 B2 *  6/2014  Wright ...................... C01B 3/56
                                         60/39.461
(Continued)

FOREIGN PATENT DOCUMENTS

CA    2 923 022    3/2015
CN    101190893   6/2008
(Continued)

OTHER PUBLICATIONS

Extended European Search Report dated Nov. 20, 2019 in corresponding European Patent Application No. 16904696.8.
(Continued)

*Primary Examiner* — Frank M Lawrence, Jr.
(74) *Attorney, Agent, or Firm* — Wenderoth, Lind & Ponack, L.L.P.

(57) ABSTRACT

A system for producing an organic substance, including: a synthesis gas generation furnace for producing a synthesis gas by partially oxidizing a waste including a carbon source; a synthesis gas purification unit connected to the synthesis gas generation furnace and purifying the synthesis gas generated in the synthesis gas generation furnace to reduce an impurity concentration in the synthesis gas; and an organic substance synthesis unit which is connected to the synthesis gas purification unit and generates an organic substance from the synthesis gas purified in the synthesis gas purification unit, wherein the synthesis gas purification unit includes a detection unit for measuring an impurity concentration in the synthesis gas.

10 Claims, 3 Drawing Sheets

(51) Int. Cl.
*C12P 7/06* (2006.01)
*C01B 3/02* (2006.01)
*C01B 3/56* (2006.01)

(52) U.S. Cl.
CPC .... *C01B 2203/042* (2013.01); *C01B 2203/06* (2013.01); *C01B 2203/1205* (2013.01); *C01B 2203/146* (2013.01); *Y02E 50/10* (2013.01)

(58) Field of Classification Search
CPC ........ C01B 2203/06; C01B 2203/1205; C01B 2203/146; C10K 1/28; C10K 1/32; C12M 47/18; C12P 7/065; Y02E 50/17
USPC ..... 95/8, 11, 96; 96/108, 111, 121, 131, 132
See application file for complete search history.

(56) References Cited

U.S. PATENT DOCUMENTS

| | | | |
|---|---|---|---|
| 2009/0211442 A1* | 8/2009 | Allam | C01B 3/36 95/96 |
| 2012/0121492 A1* | 5/2012 | Schaub | C10K 1/165 423/242.1 |
| 2014/0260989 A1* | 9/2014 | Sukhman | B01D 53/0454 96/111 |

FOREIGN PATENT DOCUMENTS

| | | |
|---|---|---|
| CN | 101538483 | 9/2009 |
| CN | 103146760 | 6/2013 |
| JP | 2006-095485 | 4/2006 |
| JP | 2012-001441 | 1/2012 |
| JP | 2012-184367 | 9/2012 |
| JP | 2016-059296 | 4/2016 |
| WO | 2011/087380 | 7/2011 |
| WO | 2016/017551 | 2/2016 |

OTHER PUBLICATIONS

International Search Report dated Nov. 1, 2016 in International (PCT) Application No. PCT/JP2016/077516, with English Translation.

Office Action and Search Report dated Jul. 1, 2020 in Chinese Patent Application No. 201680088125.1 with English-language translation of the Search Report.

* cited by examiner

SYSTEM FOR PRODUCING ORGANIC SUBSTANCE AND METHOD FOR PRODUCING ORGANIC SUBSTANCE

The present invention relates to a system for producing an organic substance and a method for producing an organic substance. Priority is claimed on PCT/JP2016/067225, filed at the Japan Patent Office on Jun. 9, 2016, the contents of which are incorporated herein by reference.

TECHNICAL FIELD

Background Art

A method is proposed, which produces an organic substance such as ethanol by allowing anaerobic microorganisms to metabolize a carbon monoxide-containing synthesis gas derived from gas discharged from manufacturing processes for chemical materials, steels or the like (see, for example, Patent Document 1).

Description of Prior Art

Patent Document

Patent Document 1: U.S. Pat. No. 8,211,679

DISCLOSURE OF INVENTION

Problems to be Solved by the Invention

However, a system for producing organic substances by microbial metabolism from synthetic gas obtained by partially oxidizing general waste collected from households, commercial establishments, etc. has the following problems.

For commercial implementation of the production, the system is desired to include a synthesis gas generation furnace that continuously feed a synthesis gas to downstream of the system; a synthesis gas purification unit for reducing the impurity concentration of the synthesis gas; and an organic substance synthesis unit for generating an organic substance by microbial metabolism from the purified synthetic gas.

In the synthesis gas generation furnace, the synthesis gas obtained by partial oxidation of the general waste includes impurities other than synthesis gas, such as hydrogen sulfide, aromatic organic compounds, oxygen and the like. Since some of these impurities are harmful to the microorganisms, it is desirable to remove such impurities in the synthesis gas purification unit.

However, since general wastes are collected from a large number of households and commercial establishments, the contents thereof are not constant, so that the composition and concentration of the impurities contained in the unpurified synthesis gas obtained by partial oxidation tend to fluctuate largely within a few minutes to several hours. For this reason, when a synthesis gas which is beyond the processing capacity of the purification apparatus constituting the synthesis gas purification unit is supplied, impurities may flow into the organic substance synthesis unit or may cause performance deterioration or breakage of the purification apparatus.

On the other hand, in order to avoid the above problem, if purification apparatuses constituting the purification unit are installed excessively in preparation for generation of larger amount of impurities than usual, the facility cost becomes excessive and the commercialization becomes difficult.

The present invention has been made in view of the above circumstances, and it is an object of the present invention to provide an organic substance production system and an organic substance production method which are capable of coping with a change in composition and concentration of impurities contained in a synthesis gas obtained by partial oxidation of waste.

Means to Solve the Problems

[1] A system for producing an organic substance, including: a synthesis gas generation furnace for producing a synthesis gas by partially oxidizing a waste including a carbon source; a synthesis gas purification unit which is connected to the synthesis gas generation furnace and purifies the synthesis gas generated in the synthesis gas generation furnace to reduce an impurity concentration in the synthesis gas; and an organic substance synthesis unit which is connected to the synthesis gas purification unit and generates an organic substance from the synthesis gas purified in the synthesis gas purification unit, wherein the synthesis gas purification unit includes: a first purification unit for purifying the synthesis gas; a second purification unit for purifying the synthesis gas purified in the first purification unit; a detection unit for measuring an impurity concentration in the synthesis gas purified in the first purification unit, wherein the detection unit is configured to: feed the synthesis gas purified in the first purification unit to a part positioned downstream of the second purification unit while bypassing the second purification unit when the impurity concentration is not higher than a predetermined value, or feed the synthesis gas purified in the first purification unit to the second purification unit when the impurity concentration is higher than the predetermined value.

[2] A system for producing an organic substance, including: a synthesis gas generation furnace for producing a synthesis gas by partially oxidizing a waste including a carbon source; a synthesis gas purification unit which is connected to the synthesis gas generation furnace and purifies the synthesis gas generated in the synthesis gas generation furnace to reduce an impurity concentration in the synthesis gas; and an organic substance synthesis unit which is connected to the synthesis gas purification unit and generates an organic substance from the synthesis gas purified in the synthesis gas purification unit, wherein the synthesis gas purification unit includes: a first purification unit for purifying the synthesis gas; a second purification unit for purifying the synthesis gas purified in the first purification unit, which has a higher ability to reduce an impurity concentration than the first purification unit; and a detection unit for measuring an impurity concentration in the synthesis gas before being purified in the first purification unit and the second purification unit, wherein the detection unit is configured to: feed the synthesis gas to the first purification unit when the impurity concentration is not higher than a predetermined value, or feed the synthesis gas to the second purification unit when the impurity concentration is higher than the predetermined value.

[3] A system for producing an organic substance, including: a synthesis gas generation furnace for producing a synthesis gas by partially oxidizing a waste including a carbon source; a synthesis gas purification unit connected to the synthesis gas generation furnace and purifying the synthesis gas generated in the synthesis gas generation furnace to reduce an impurity concentration in the synthesis gas; and an organic substance synthesis unit connected to the synthesis gas purification unit to generate an organic substance from the synthesis gas purified in the synthesis gas purification unit, wherein the synthesis gas purification unit includes: a first purification unit for purifying the synthesis gas; a second purification unit for purifying the synthesis gas purified in the first purification unit; a mixing unit for sequentially receiving the synthesis gas from the first purification unit, mixing together the synthesis gas received earlier and the synthesis gas received later, and feeding resulting synthesis gas to the second purification unit; and a detection unit for measuring an impurity concentration in the synthesis gas purified in the first purification unit, wherein the detection unit is configured to: feed the synthesis gas purified in the first purification unit to the second purification unit or the mixing unit when the impurity concentration is not higher than a predetermined value, or feed the synthesis gas purified in the first purification unit to the mixing unit when the impurity concentration is higher than the predetermined value, to thereby mix the synthesis gas with the synthesis gas with an impurity concentration not higher than the predetermined value.

[4] A system for producing an organic substance, including: a synthesis gas generation furnace for producing a synthesis gas by partially oxidizing a waste including a carbon source; a synthesis gas purification unit connected to the synthesis gas generation furnace and purifying the synthesis gas generated in the synthesis gas generation furnace to reduce an impurity concentration in the synthesis gas; and an organic substance synthesis unit connected to the synthesis gas purification unit to generate an organic substance from the synthesis gas purified in the synthesis gas purification unit, wherein the synthesis gas purification unit includes: a first purification unit for purifying the synthesis gas; a second purification unit for purifying the synthesis gas purified in the first purification unit; a detection unit for measuring an impurity concentration in the synthesis gas purified in the first purification unit, wherein the detection unit is configured to: feed the synthesis gas purified in the first purification unit to the second purification unit when the impurity concentration is not higher than a predetermined value, or return the synthesis gas purified in the first purification unit to the first purification unit or the synthesis gas generation furnace when the impurity concentration is higher than a predetermined value.

[5] The system according to any one of [1] to [4], wherein the predetermined value of the impurity concentration is in a range of concentration that adversely affects anaerobic bacteria that produce the organic substance in the organic substance synthesis unit.

[6] The system according to any one of [1] to [5], wherein the first purification unit is a pressure swing adsorption apparatus or a temperature swing adsorption apparatus. [7] The system according to any one of [1] to [6], wherein the second purification unit includes activated carbon.

[8] A method for producing an organic substance using the organic substance production system according to [1], which includes: a step of generating a synthesis gas in the synthesis gas generation furnace; a step of purifying the synthesis gas in the synthesis gas purification unit; and a step of generating an organic substance from the purified synthesis gas in the organic substance synthesis unit, wherein the step of purifying the synthesis gas purification includes: a step of purifying the synthesis gas in the first purification unit; a step of measuring an impurity concentration in the synthesis gas purified in the first purification unit by the detection unit, a step of: feeding the synthesis gas purified in the first purification unit to a part positioned downstream of the second purification unit while bypassing the second purification unit when the impurity concentration is not higher than a predetermined value, or feeding the synthesis gas purified in the first purification unit to the second purification unit when the impurity concentration is higher than the predetermined value, thereby purifying synthesis gas in the second purification unit, and feeding the synthesis gas purified in the second purification unit to a part positioned downstream of the second purification unit.

[9] A method for producing an organic substance using the organic substance production system according to [2], which includes: a step of generating a synthesis gas in the synthesis gas generation furnace; a step of purifying the synthesis gas in the synthesis gas purification unit; and a step of generating an organic substance from the purified synthesis gas in the organic substance synthesis unit, wherein the step of purifying the synthesis gas purification includes: a step of measuring an impurity concentration in the synthesis gas by the detection unit, a step of: feeding the synthesis gas to the first purification unit when the impurity concentration is not higher than a predetermined value, thereby purifying the synthesis gas, or feeding the synthesis gas to the second purification unit when the impurity concentration is higher than a predetermined value, thereby purifying the synthesis gas.

[10] A method for producing an organic substance using the organic substance production system according to [3], which includes: a step of generating a synthesis gas in the synthesis gas generation furnace; a step of purifying the synthesis gas in the synthesis gas purification unit; and a step of generating an organic substance from the purified synthesis gas in the organic substance synthesis unit, wherein the step of purifying the synthesis gas purification includes: a step of purifying the synthesis gas in the first purification unit; a step of measuring an impurity concentration in the synthesis gas purified in the first purification unit by the detection unit, and a step of: feeding the synthesis gas purified in the first purification unit to the second purification unit or the mixing unit when the impurity concentration is not higher than a predetermined value, or feeding the synthesis gas purified in the first purification unit to the mixing unit when the impurity concentration is higher than the predetermined value, to thereby mix the synthesis gas with the synthesis gas with an impurity concentration not higher than the predetermined value.

[11] A method for producing an organic substance using the organic substance production system according to [4], which includes: a step of generating a synthesis gas in the synthesis gas generation furnace; a step of purifying the synthesis gas in the synthesis gas purification unit; and a step of generating an organic substance from the purified synthesis gas in the organic substance synthesis unit, wherein the step of purifying the synthesis gas purification includes: a step of purifying the synthesis gas in the first purification unit; a step of measuring an impurity concentration in the synthesis gas purified in the first purification unit by the detection unit, and a step of: feeding the synthesis gas purified in the first purification unit to the second purification unit when the impurity concentration is not higher than a predetermined value, or returning the synthesis gas purified in the first purification unit to the first purification unit or the synthesis gas generation furnace when the impurity concentration is higher than a predetermined value.

[12] The method according to any one of [8] to [11], wherein the predetermined value of the impurity concentration is in a range of concentration that adversely affects anaerobic bacteria that produce the organic substance in the organic substance synthesis unit.

Effect of the Invention

According to the organic substance production system and organic substance production method of the present invention, it is possible to detect fluctuations in composition and concentration of impurities contained in an unpurified synthesis gas obtained by partial oxidation of waste, and to promptly change the process flow in the purification unit in accordance with the fluctuation, whereby the impurity concentration can be reduced with an optimum device configuration. This makes it possible to easily commercialize the organic substance production system and method of the present invention.

DESCRIPTION OF THE EMBODIMENTS

Hereinbelow, examples of the preferred embodiments of the present invention are described, referring to the annexed drawings. In the drawings, components having substantially the same functions are denoted with the same reference numerals.

《First Embodiment》

<Organic Substance Production System 10>

Figure 1:
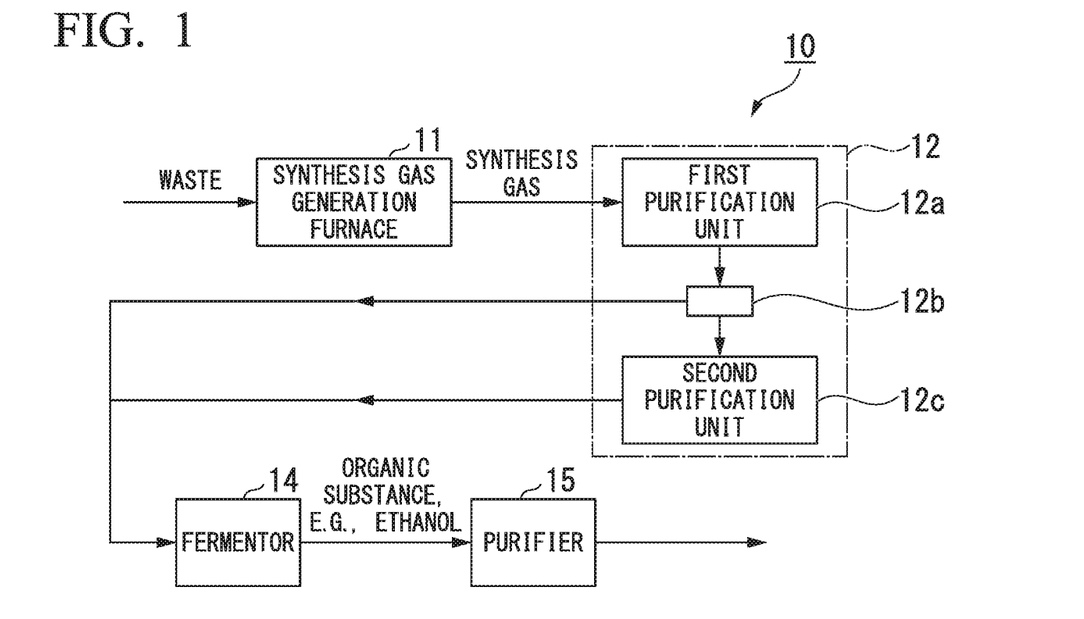
FIG. 1 is a schematic view of the organic substance production system 10 according to the first embodiment of the present invention.

As shown in FIG. 1, the organic substance production system 10 according to the first embodiment of the present invention includes: a synthesis gas generation furnace 11 for producing a synthesis gas by partially oxidizing a waste including a carbon source; a synthesis gas purification unit 12 which is connected to the synthesis gas generation furnace 11 and purifies the synthesis gas generated in the synthesis gas generation furnace 11 to reduce an impurity concentration in the synthesis gas; and an organic substance synthesis unit 14 which is connected to the synthesis gas purification unit 12 and generates an organic substance from the synthesis gas purified in the synthesis gas purification unit 12.

The waste used to obtain the synthesis gas in the synthesis gas production furnace 11 is not particularly limited as long as it contains a carbon source. Examples of the waste include those which can be incinerated, such as domestic waste and general industrial waste. Examples of the carbon source include resin waste materials such as plastic and rubber. As the synthesis gas generation furnace 11, any known furnaces which can generate a synthesis gas by partial oxidation of the waste can be used. Generally, the synthesis gas obtained by partial oxidation of the waste contains carbon monoxide, hydrogen gas, nitrogen gas and the like.

The synthesis gas obtained in the synthesis gas generation furnace 11 may contain impurities, examples of which include as hydrogen sulfide, carbonyl oxide, NOx, SOx, hydrogen fluoride, oxygen, ammonia, hydrogen cyanide, hydrocarbons such as methane, propane, propylene, acetylene, ethylene, ethane, isobutane and the like, aliphatic oxygen compounds such as dimethyl ether, formaldehyde, methyl formate and the like, aromatic organic compounds such as benzene, toluene, xylene, methylbenzene, naphthalene and the like, and tar. The type and concentration of impurities can vary greatly depending on the type of waste to be partially oxidized.

In the synthesis gas purification unit 12 to which the synthesis gas generated in the synthesis gas generation furnace 11 is fed, two or more known purification apparatuses for reducing the concentration of one or more types of the above-mentioned impurities contained in the synthesis gas are provided.

The synthesis gas purification unit 12 includes a first purification unit 12a for purifying the synthesis gas, a second purification unit 12c for purifying the synthesis gas purified by the first purification unit 12a, and a detection unit 12b for measuring the impurity concentration in the synthesis gas purified by the first purification unit 12a.

The purification units provided in the synthesis gas purification unit 12 are connected by piping indicated by arrows in the drawing. The detection unit 12b is connected via piping between the first purification unit 12a, the second purification unit 12c and the organic substance synthesis unit 14, and a pipe on the downstream side of the detection unit 12b is branched. The first purification unit 12a is connected to the second purification unit 12c and the organic substance synthesis unit 14 via the detection unit 12b. The second purification unit 12c is connected to the detection unit 12b and the organic substance synthesis unit 14.

The synthesis gas from the synthesis gas generation furnace 11 is first purified in the first purification unit 12a, and its impurity concentration is reduced. Then, the synthesis gas is fed to the detection unit 12b.

The detection unit 12b measures an impurity concentration in the synthesis gas fed from the first purification unit 12a. When the impurity concentration is not higher than a predetermined value (predetermined threshold value), the detection unit 12b feeds the synthesis gas purified by the first purification unit 12a into a fermenter of the organic substance synthesis unit 14 positioned downstream of the second purification unit 12c, while bypassing the second purification unit 12c. On the other hand, when the impurity concentration is higher than the predetermined value, the detection unit 12b sends the synthesis gas purified by the first purification unit 12a to the second purification unit 12c.

The above-stated predetermined value of the impurity concentration can be defined, for example, as a range of concentration that is known to adversely affect the microorganisms that produce the organic substance in the organic substance synthesis unit 14 with respect to each of various impurities. The concentration range is determined in view of a combination of the type of impurities and the type of microorganisms. The expression "adversely affect" refers to any undesirable phenomena such as microbial death, decreased proliferative ability, decreased utilization rate, decreased productivity of a substance of interest, and the like.

Examples of impurities which adversely affect microorganisms such as anaerobic bacteria which produce an organic substance from the synthesis gas include methane, acetylene, ethylene, ethane, tar, benzene, toluene, ethylbenzene, xylene, ammonia, hydrogen cyanide, NOx, hydrogen sulfide, carbonyl sulfide, naphthalene and the like. As a concentration at which the impurities adversely affect microorganisms, for example, it has been reported that an acetylene concentration of 1 ppm or more or an ethylene concentration of 1 ppm or more in the synthesis gas has an adverse effect on *Clostridium* bacteria (U.S. Pat. No. 9,011,578 B2). Therefore, one or more types of the impurities and the concentration range thereof can be appropriately set according to the operating conditions of the organic substance production system 10.

For example, specific impurities and concentrations adversely affecting microorganisms of the genus *Clostridium* may be as follows: acetylene: 5 ppm or more, ethylene: 50 ppm or more, HCN: 2 ppm or more, benzene: 1 ppm or more (U.S. Pat. No. 9,011,578 B2), NOx: 150 ppm or more (AIMS Bioengineering, 3(2): 188-210) and the like. However, these impurities and the concentration ranges thereof are mere examples, and other impurities and concentration ranges are also applicable.

The second purification unit 12c purifies the fed synthesis gas and feeds the resulting synthesis gas having a reduced impurity concentration to the fermenter.

In the production system 10, the first purification unit 12a and the second purification unit 12c are provided. Unless the impurity concentration is higher than the predetermined value, only the first purification unit 12a is used. The second purification unit 12c is used only when the impurity concentration is higher than the predetermined value. Therefore, the impurity concentration reducing ability (purifying capacity) of the first purification unit 12a need not be higher, or may be even lower, than the impurity concentration reducing ability of the second purification unit 12c.

Thus, according to the production system 10, it is possible to reduce the running cost of the synthesis gas purification unit 12, as compared to the case of providing one high-performance or large-scale purification unit for coping with the case where the concentration of impurities contained in the synthesis gas becomes extremely high.

From the viewpoint of suppressing the running cost of the synthesis gas purification unit 12 to further lower level, it is preferable that the first purification unit 12a is a pressure swing adsorption apparatus (PSA) or a temperature swing adsorption apparatus (TSA), which can be operated at a low running cost. On the other hand, in order to surely suppress the supply of the synthesis gas having a high impurity concentration to the organic substance synthesis unit 14, it is preferable that the second purification unit 12c is an apparatus including activated carbon, which has a higher impurity concentration reducing ability than PSA and TSA. For example, when an aromatic compound such as benzene is taken as an example of the impurities, the activated carbon has a higher running cost than the above-mentioned PSA or the like, but has excellent benzene removing ability. Therefore, the activated carbon is expected to be capable of suppressing the concentration of the aromatic compound contained as an impurity in the synthesis gas to a lower level.

The synthesis gas purified by the synthesis gas purification unit 12 is fed to a fermentor (microorganism incubator) of the organic substance synthesis unit 14. The microorganisms in the fermentor metabolize the synthesis gas to produce an organic substance. Here, the term "metabolize" embraces the concept of fermentation. Specific examples of the microorganisms suitably used in the case of producing alcohols such as ethanol include anaerobic carboxydotrophic bacteria and the like. More specific examples include anaerobic bacteria such as *Clostridium* bacteria, *Moorella* bacteria, Acetobacterium bacteria, *Carboxydocella sporoducens* sp. Nov., *Rhodopseudomonas gelatinosa*, *Eubacterium limosum*, and *Butyribacterium methylotrophicum*.

Examples of the *Clostridium* bacteria include *Clostridium ljungdahlii*, *Clostridium autoethanogenum*, *Clostridium carboxidivorans*, *Clostridium ragsdalei* (Kopke M. et al., Appl. Environ. Microbiol. 2011, 77 (15), 5467-5475), and *Clostridium thermoaceticum*. Examples of the *Moorella* bacteria include *Moorella thermoacetica* (Pierce EG. Et al., Environ. Microbiol. 2008, 10, 2550-2573). Examples of the Acetobacterium bacteria include Acetobacterium woodii (Dilling S. et al., Appl. Environ. Microbiol. 2007, 73 (11), 3630-3636).

The organic substance synthesis unit 14 is connected to a purifier 15 for obtaining an organic substance of interest from various organic substances generated by microorganisms. The product in the organic substance synthesis unit 14 is transferred to a purifier 15 and an organic substance of interest is obtained by a known purification method.

Examples of the organic substances produced by the production system 10 include alcohols, organic acids, fatty acids, fats and oils, ketones, biomass, sugars and the like. More specific examples include ethanol, acetic acid, butanediol and the like. The use of the produced organic substance is not particularly limited, and examples thereof include raw materials for resins such as plastics and rubbers, and fuels.

Other Embodiments

The detector constituting the detection unit 12b in the production system 10 described above is connected between the first purification unit 12a and the second purification unit 12c. However, the detector is not limited to be one which is connected between the first purification unit 12a and the second purification unit 12c, and may be of any configuration as long as the detector is connected so as to be able to detect (measure) the impurity concentration of the synthesis gas purified by the first purification unit 12a. For example, the detector may be connected to only the first purification unit 12a, while allowing a regulator (other than the detector) constituting the detection unit 12b to distribute the synthesis gas purified by the first purification unit 12a.

In the synthesis gas purification unit 12, in addition to the two purification units 12a and 12c, another purification unit may be provided upstream of the first purification unit 12a or downstream of the second purification unit 12c.

<Organic Substance Production Method 10>

A method 10 which can be mentioned as an example of embodiments in which an organic substance is produced using the organic substance production system 10 includes a step of generating the synthesis gas in the synthesis gas generation furnace 11, a step of purifying the synthesis gas in the synthesis gas purification unit 12, and a step of generating an organic substance from the purified synthesis gas in the organic substance synthesis unit 14.

In the production method 10, the step of purifying the synthesis gas includes a step of purifying the synthesis gas in the first purification section 12a, a step of measuring the impurity concentration in the synthesis gas purified in the first purification section 12*a* by the detection unit 12*b* (detection step).

When the impurity concentration is not higher than the predetermined value, the synthesis gas purified by the first purification unit 12*a* is fed into a fermentor of the organic substance synthesis unit 14 positioned downstream of the second purification unit 12*c*, while bypassing the second purification unit 12*c*. On the other hand, when the impurity concentration is higher than the predetermined value, the synthesis gas purified by the first purification unit 12*a* is fed into the second purification unit 12*c* to further purify the synthesis gas, and the synthesis gas purified by the second purification unit 12*c* is fed to the fermentor of the organic substance synthesis unit 14 positioned downstream of the second purification unit 12*c*.

The predetermined value of the impurity concentration can be set, for example, in view of the adverse effect on the microorganisms as described above.

According to the production method 10, it is possible to determine whether or not to use the second purification unit 12*c* depending on the impurity concentration measured in the detection step. Therefore, it is unnecessary to constantly operate the second purification unit 12*c*, which has a high impurity concentration reducing ability and is likely to increase cost, whereby the frequency of replacement and maintenance of the second purification unit 12*c* can be reduced and the running cost of the synthesis gas purification unit 12 can be reduced accordingly.

《Second Embodiment》

<Organic Substance Production System 20>

Figure 2:
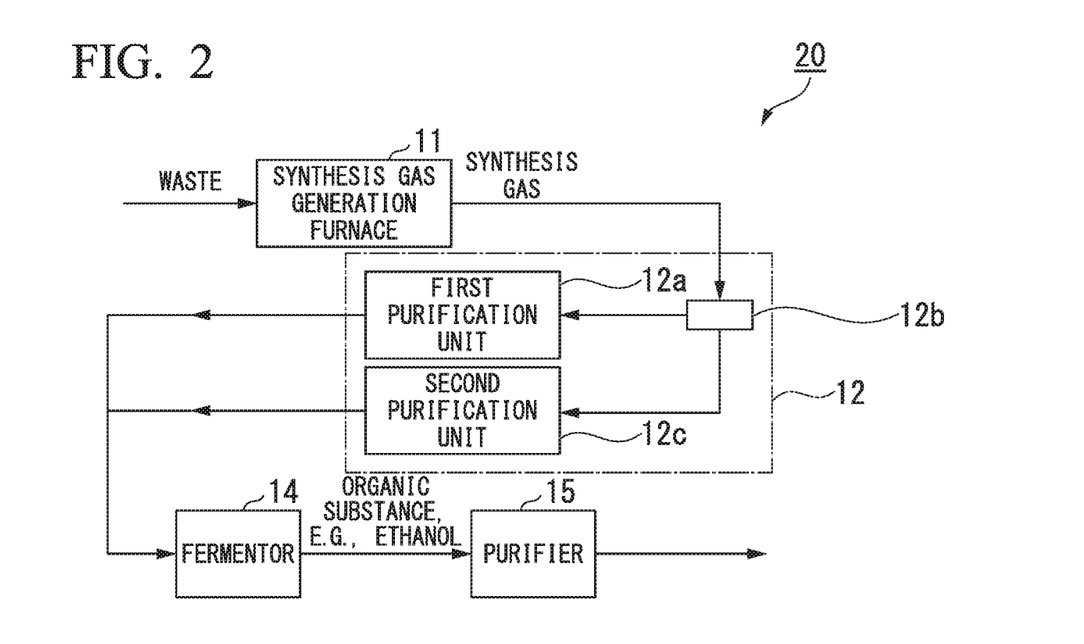
FIG. 2 is a schematic view of the organic substance production system 20 according to the second embodiment of the present invention.

As shown in FIG. 2, the organic substance production system 20 of the second embodiment of the present invention includes a synthesis gas generation furnace 11, a synthesis gas purification unit 12, and an organic substance synthesis unit 14. In this respect, the production system 30 is the same as the production system 10.

The synthesis gas purification unit 12 has two purification units that purify the synthesis gas generated in the synthesis gas generation furnace 11, that is, the first purification unit 12*a* and the second purification unit 12*c* having a higher impurity concentration reducing ability than the first purification unit 12*a*. Furthermore, the synthesis gas purification unit 12 has a detection unit 12*b* that measures the concentration of impurities contained in the synthesis gas before being purified by the first purification unit 12*a* and the second purification unit 12*c*.

The purification units provided in the synthesis gas purification unit 12 are connected by piping indicated by arrows in the drawing. The detection unit 12*b* is connected via piping between the synthesis gas generation furnace 11, the first purification unit 12*a* and the second purification unit 12*c*, and a pipe on the downstream side of the detection unit 12*b* is branched. The first purification unit 12*a* and the second purification unit 12*c* are connected in parallel on the downstream side of the detection unit 12*b*. The synthesis gas generation furnace 11 is connected to the first purification unit 12*a* and the second purification unit 12*c* via the detection unit 12*b*. The first purification unit 12*a* and the second purification unit 12*c* are independently connected to the detection unit 12*b* and the organic substance synthesis unit 14.

The synthesis gas from the synthesis gas generation furnace 11 is first fed to the detection unit 12*b*.

The detection unit 12*b* measures the impurity concentration in the synthesis gas from the synthesis gas generation furnace 11. When the impurity concentration is not higher than a predetermined value (predetermined threshold value), the detection unit 12*b* feeds the synthesis gas into the first purification unit 12*a* having a lower impurity concentration reducing ability than the second purification unit 12*c*. On the other hand, when the impurity concentration is higher than the predetermined value, the synthesis gas is fed to the second purification unit 12*c* having a relatively high impurity concentration reducing ability.

The first purification unit 12*a* and the second purification unit 12*c* purify the fed synthesis gas and feed the resulting synthesis gas having a reduced impurity concentration to the fermentor.

In the production system 20, the first purification unit 12*a* and the second purification unit 12*c* can be selectively used according to the impurity concentration in the synthesis gas supplied from the synthesis gas generation furnace 11. Therefore, the impurity concentration reducing ability of the first purification unit 12*a* need not be higher, or may be even lower, than the impurity concentration reducing ability of the second purification unit 12*c*.

Thus, according to the production system 20, it is possible to reduce the running cost of the synthesis gas purification unit 12, as compared to the case of providing one high-performance or large-scale purification unit for coping with the case where the concentration of impurities contained in the synthesis gas becomes extremely high.

The predetermined value of the impurity concentration can be set, for example, in view of the adverse effect on the microorganisms as described above.

Other Embodiments

The detector constituting the detection unit 12*b* in the production system 20 described above is connected between the synthesis gas generation furnace 11 and the two purification units 12*a*,12*c*. However, the detector is not limited to be one which is connected between the synthesis gas generation furnace 11 and the two purification units 12*a*,12*c*, and may be of any configuration as long as the detector is connected so as to be able to detect (measure) the impurity concentration of the synthesis gas before being purified by the two purification units 12*a*, 12*c*. For example, the detector may be connected to only the synthesis gas generation furnace 11, while allowing a regulator (other than the detector) constituting the detection unit 12*b* to distribute the synthesis gas generated by the synthesis gas generation furnace 11.

In the synthesis gas purification unit 12, in addition to the two purification units 12*a* and 12*c*, another purification unit may be provided upstream of the detection unit 12*b* or downstream of the first purification unit 12*a* and the second purification unit 12*c*.

<Organic Substance Production Method 20>

A method 20 which can be mentioned as an example of embodiments in which an organic substance is produced using the organic substance production system 20 includes a step of generating the synthesis gas in the synthesis gas generation furnace 11, a step of purifying the synthesis gas in the synthesis gas purification unit 12, and a step of generating an organic substance from the purified synthesis gas in the organic substance synthesis unit 14.

In the synthesis gas purification step, first, a step of measuring the impurity concentration in the synthesis gas from the synthesis gas generation furnace 11 by the detection unit 12b (detection step) is performed.

When the impurity concentration measured in the detection step is not higher than a predetermined value, the synthesis gas is fed to the first purification unit 12a to purify the synthesis gas. On the other hand, when the impurity concentration measured in the detection step is higher than the predetermined value, the synthesis gas is fed to the second purification unit 12c having a higher impurity concentration reducing ability than the first purification unit 12a, to reduce the impurity concentration of the synthesis gas.

The predetermined value of the impurity concentration can be set, for example, in view of the adverse effect on the microorganisms as described above.

According to the production method 20, it is possible to determine whether the first purification unit 12a or the second purification unit 12c should be used depending on the level of impurity concentration measured in the detection step. Therefore, it is unnecessary to constantly operate the second purification unit 12c, which has a high impurity concentration reducing ability and is likely to increase cost, whereby the frequency of replacement and maintenance of the second purification unit 12c can be reduced and the running cost of the synthesis gas purification unit 12 can be reduced accordingly.

《 Third Embodiment 》

<Organic Substance Production System 30>

Figure 3:
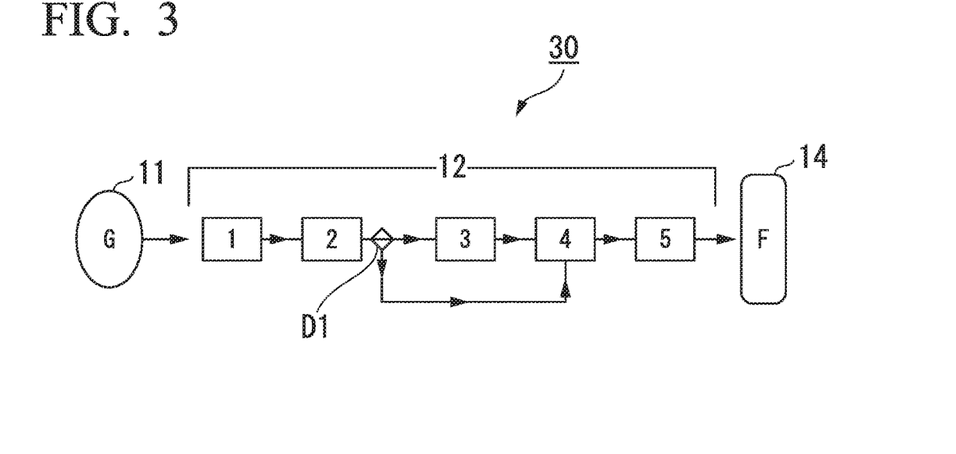
FIG. 3 is a schematic view of the organic substance production system 30 according to the third embodiment of the present invention.

As shown in FIG. 3, the organic substance production system 30 of the third embodiment of the present invention includes a synthesis gas generation furnace 11, a synthesis gas purification unit 12, and an organic substance synthesis unit 14. In this respect, the production system 30 is the same as the production system 10.

The synthesis gas purification unit 12 includes a scrubber 1, a gas chiller 2, a desulfurization tank 3, a pressure swing adsorption apparatus (PSA) 4, and an activated carbon tank 5, which are sequentially connected between the synthesis gas generation furnace 11 and the organic substance synthesis unit 14. These are connected via piping denoted by arrows in the drawing.

Examples of liquids usable for the scrubber 1 include water, an acid, an alkali, and an organic solvent, and water is particularly preferable as the scrubbing liquid.

The synthesis gas purification unit 12 has a detector D1. The detector D1 is connected via piping between the gas chiller 2 and the desulfurization tank 3, and the pipe on the downstream side of the detector D1 is branched. The gas chiller 2 is connected to the desulfurization tank 3 and the PSA 4 via the detector D1.

<Organic Substance Production Method 30>

Using the organic substance production system 30, an organic substance can be produced in the same manner as in the case of the production system 10 described above.

Specifically, first, the synthesis gas fed from the synthesis gas generation furnace 11 is treated with the scrubber 1 to thereby reduce the concentration of impurities, such as HCN, $NH_3$ and soot, contained in the synthesis gas. Next, treatment with the gas chiller 2 is carried out to reduce the concentration of impurities such as moisture mixed into the gas in the scrubber 1 of the preceding stage, and naphthalene which easily solidifies.

Subsequently, the concentration of impurities such as $H_2S$ contained in the synthesis gas treated by the gas chiller 2 is measured by the detector D1.

When the impurity concentration is not higher than a predetermined value, the synthesis gas is fed to the PSA 4 provided downstream of the desulfurization tank 3 while bypassing the desulfurization tank 3. On the other hand, when the impurity concentration is higher than the predetermined value, the synthesis gas is fed into the desulfurization tank 3 to reduce the concentrations of impurities such as $H_2S$, and the resulting purified synthesis gas is fed to the PSA 4 installed downstream of the organic substance synthesis unit 14.

In the method exemplified above, at least one of the scrubber 1 and the gas chiller 2 is the first purification unit 12a and the desulfurization tank 3 is the second purification unit 12c.

The predetermined value of the impurity concentration can be set, for example, in view of the adverse effect on the microorganisms as described above.

Besides being capable of removing $H_2S$, the PSA 4 can also reduce the concentration of impurities such as $H_2O$, $CO_2$, benzene, toluene and xylene.

Supplying a high concentration $H_2S$ to the PSA 4 should be avoided, as it leads to performance degradation of the PSA 4 and the activated carbon provided downstream.

Subsequently, the synthesis gas treated in the PSA 4 is treated in the activated carbon tank 5 and, if necessary, subjected to further treatment with another purification apparatus (not shown) to reduce the concentration of various remaining impurities left unremoved in the preceding processes. The resulting synthesis gas is fed to the organic substance synthesis unit 14.

《 Fourth Embodiment 》

<Organic Substance Production System 40>

Figure 4:
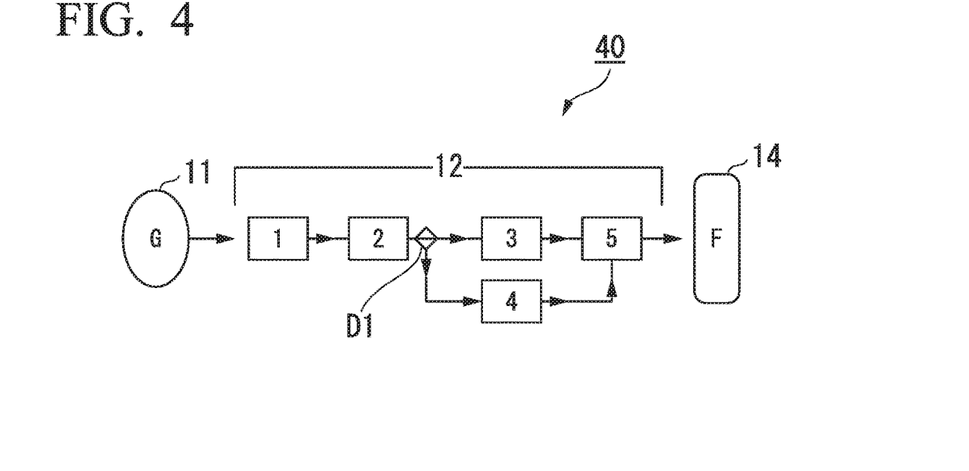
FIG. 4 is a schematic view of the organic substance production system 40 according to the fourth embodiment of the present invention.

As shown in FIG. 4, the organic substance production system 40 of the fourth embodiment of the present invention includes a synthesis gas generation furnace 11, a synthesis gas purification unit 12, and an organic substance synthesis unit 14. In this respect, the production system 40 is the same as the production system 20.

The synthesis gas purification unit 12 includes a scrubber 1, a gas chiller 2, a desulfurization tank 3, a pressure swing adsorption apparatus (PSA) 4, and an activated carbon tank 5, which are sequentially connected between the synthesis gas generation furnace 11 and the organic substance synthesis unit 14. These are connected via piping denoted by arrows in the drawing.

The synthesis gas purification unit 12 has a detector D1. The detector D1 is connected via piping between the desulfurization tank 3 and the PSA 4, and the pipe on the downstream side of the detector D1 is branched. The gas chiller 2 is connected to the desulfurization tank 3 and the PSA 4 via the detector D1. The desulfurization tank 3 and the PSA 4 are connected to the activated carbon tank 5.

<Organic Substance Production Method 40>

Using the organic substance production system 40, an organic substance can be produced in the same manner as in the case of the production system 20 described above.

Specifically, first, the synthesis gas from the synthesis gas generation furnace 11 is treated with the scrubber 1 and the gas chiller 2, and then the concentration of impurities, such as $H_2S$, contained in the obtained synthesis gas is measured by the detector D1.

When the impurity concentration is not higher than the predetermined value, the synthesis gas is fed into the PSA 4 to reduce the impurity concentration of the synthesis gas. On the other hand, when the impurity concentration is higher than the predetermined value, the synthesis gas is fed to the desulfurization tank 3 having a higher $H_2S$ reducing ability than the PSA 4 to reduce the impurity concentration of the synthesis gas.

In the method exemplified above, the PSA 4 is the first purification unit 12a and the desulfurization tank 3 is the second purification unit 12c, when classified in terms of the $H_2S$ reducing ability.

The predetermined value of the impurity concentration can be set, for example, in view of the adverse effect on the microorganisms as described above.

Subsequently, the synthesis gas treated in the desulfurization tank 3 or the PSA 4 is treated in the activated carbon tank 5 and, if necessary, further transferred to and treated in another purification apparatus (not shown) to reduce the concentration of the impurities. The resulting synthesis gas is fed to the organic substance synthesis unit 14.

《Fifth Embodiment》

<Organic Substance Production System 50>

Figure 5:
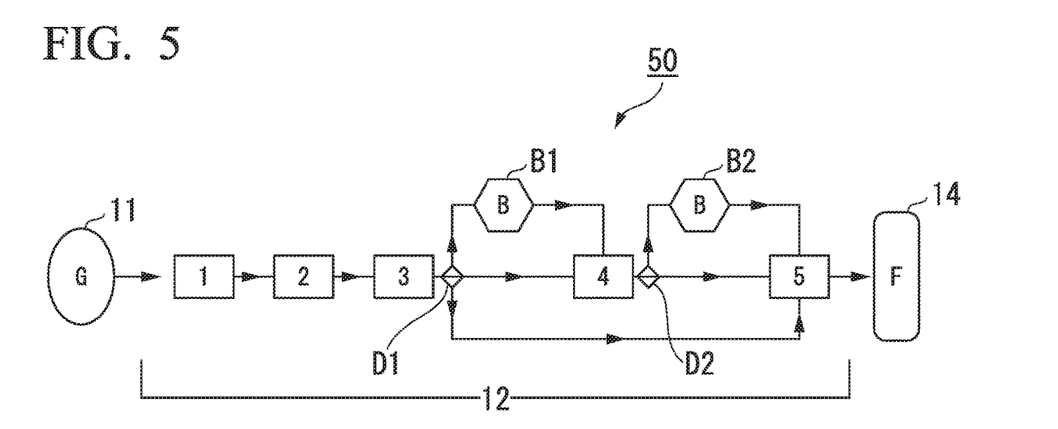
FIG. 5 is a schematic view of the organic substance production system 50 according to the fifth embodiment of the present invention.

As shown in FIG. 5, the organic substance production system 50 of the fifth embodiment of the present invention includes a synthesis gas generation furnace 11, a synthesis gas purification unit 12, and an organic substance synthesis unit 14. In this respect, the production system 50 is the same as the production systems 10, 20, 30 and 40.

The synthesis gas purification unit 12 includes: a first purification unit for purifying the synthesis gas generated in the synthesis gas generation furnace 11; a second purification unit for purifying the synthesis gas purified by the first purification unit; a mixing unit for sequentially receiving the synthesis gas from the first purification unit, mixing together the synthesis gas received earlier and the synthesis gas received later, and feeding the resulting synthesis gas to the second purification unit; and a detection unit for measuring the impurity concentration in the synthesis gas purified by the first purification unit.

When the impurity concentration is not higher than a predetermined value, the detection unit feeds the synthesis gas purified in the first purification unit to the second purification unit or the mixing unit. On the other hand, when the impurity concentration is higher than the predetermined value, the detection unit feeds the synthesis gas purified in the first purification unit to the mixing unit, to thereby mix the synthesis gas with the synthesis gas having an impurity concentration not higher than the predetermined value.

The predetermined value of the impurity concentration can be set, for example, in view of the adverse effect on the microorganisms as described above.

The synthesis gas purification unit 12 of the production system 50 includes a scrubber 1, a gas chiller 2, a desulfurization tank 3, a PSA 4, an activated carbon tank 5, a first dilution tank B1, a second dilution tank B2, a first detector D1, and a second detector D2, which are sequentially connected between the synthesis gas generation furnace 11 and the organic substance synthesis unit 14. These are connected via piping denoted by arrows in the drawing.

<Organic Substance Production Method 50>

A method 50 which can be mentioned as an example of embodiments in which an organic substance is produced using the organic substance production system 50 includes a step of generating the synthesis gas in the synthesis gas generation furnace 11, a step of purifying the synthesis gas in the synthesis gas purification unit 12, and a step of generating an organic substance from the purified synthesis gas in the organic substance synthesis unit 14.

In the synthesis gas purification step, first, a step of purifying the synthesis gas from the synthesis gas generation furnace 11 with the first purification unit to reduce the impurity concentration of the synthesis gas in the first purification unit, and a step of measuring the impurity concentration in the synthesis gas purified in the first purification unit by the detection unit (detection step) are performed.

When the impurity concentration is not higher than a predetermined value, the synthesis gas purified in the first purification unit is fed to the second purification unit or the mixing unit. On the other hand, when the impurity concentration is higher than the predetermined value, the synthesis gas purified in the first purification unit is fed to the mixing unit, to thereby mix the synthesis gas with the synthesis gas having an impurity concentration not higher than the predetermined value.

A specific example of an embodiment in which an organic substance is produced using the organic substance production system 50 will be described below.

First, the synthesis gas from the synthesis gas generation furnace 11 is treated with the scrubber 1, the gas chiller 2 and the desulfurization tank 3, and then the concentration of impurities, such as $H_2S$, contained in the obtained synthesis gas is measured by the detector D1.

When the impurity concentration is not higher than the predetermined value, the synthesis gas is fed into the PSA 4 or the activated carbon tank 5, or the synthesis gas is fed into the first dilution tank B1.

When the impurity concentration is higher than the predetermined value, the synthesis gas is fed into the first dilution tank B1 and mixed with a synthesis gas having an impurity concentration not higher than the predetermined value. The above-stated synthesis gas having an impurity concentration not higher than the predetermined value, which is to be mixed here, may be a pre-fed synthesis gas that has been fed to the first dilution tank B1 beforehand, or a post-fed synthesis gas having an impurity concentration not higher than the predetermined value, which is fed later to the first dilution tank B1.

By sequentially receiving the synthesis gas from the desulfurization tank 3 at the first dilution tank B1 to allow homogenization of the composition of the resulting synthesis gas mixture in the first dilution tank B1, highly concentrated impurities that are suddenly or temporarily generated can be diluted. The synthesis gas mixture is fed from the first dilution tank B1 to the PSA 4.

According to the above configuration, it is possible to prevent the highly concentrated impurities having passed through the desulfurization tank 3 from inflicting irreparable damage on the purification apparatus provided downstream.

In the method exemplified above, any one or more of the scrubber 1, the gas chiller 2 and the desulfurization tank 3 is the first purification unit, and the PSA 4 is the second purification unit.

Subsequently, as shown in FIG. 5, the concentration of various impurities contained in the synthesis gas from the PSA 4 is measured by the second detector D2.

When the impurity concentration is not higher than the predetermined value, the synthesis gas is fed into the activated carbon tank 5, or the synthesis gas is fed into the second dilution tank B2.

When the impurity concentration is higher than the predetermined value, the synthesis gas is fed into the second dilution tank B2 and mixed with a synthesis gas having an impurity concentration not higher than the predetermined value. The above-stated synthesis gas having an impurity concentration not higher than the predetermined value, which is to be mixed here, may be a pre-fed synthesis gas that has been fed to the second dilution tank B2 beforehand, or a post-fed synthesis gas having an impurity concentration not higher than the predetermined value, which is fed later to the second dilution tank B2.

The predetermined value of the impurity concentration can be set, for example, in view of the adverse effect on the microorganisms as described above.

By sequentially receiving the synthesis gas from the PSA 4 at the second dilution tank B2 to allow homogenization of the composition of the resulting synthesis gas mixture in the second dilution tank B2, highly concentrated impurities that are suddenly or temporarily generated can be diluted. The synthesis gas mixture is fed from the second dilution tank B2 to the activated carbon tank 5.

According to the above configuration, it is possible to prevent the highly concentrated impurities having passed through the PSA 4 from inflicting irreparable damage on the purification apparatus provided downstream.

In the method exemplified above, any one or more of the scrubber 1, the gas chiller 2, the desulfurization tank 3, and the PSA 4 is the first purification unit, and the activated carbon tank 5 is the second purification unit.

Subsequently, the synthesis gas treated in the desulfurization tank 3 or the PSA 4 is treated in the activated carbon tank 5 and, if necessary, further transferred to and treated in another purification apparatus (not shown) to reduce the concentration of the impurities. The resulting synthesis gas is fed to the organic substance synthesis unit 14.

《Sixth Embodiment》

<Organic Substance Production System 60>

Figure 6:
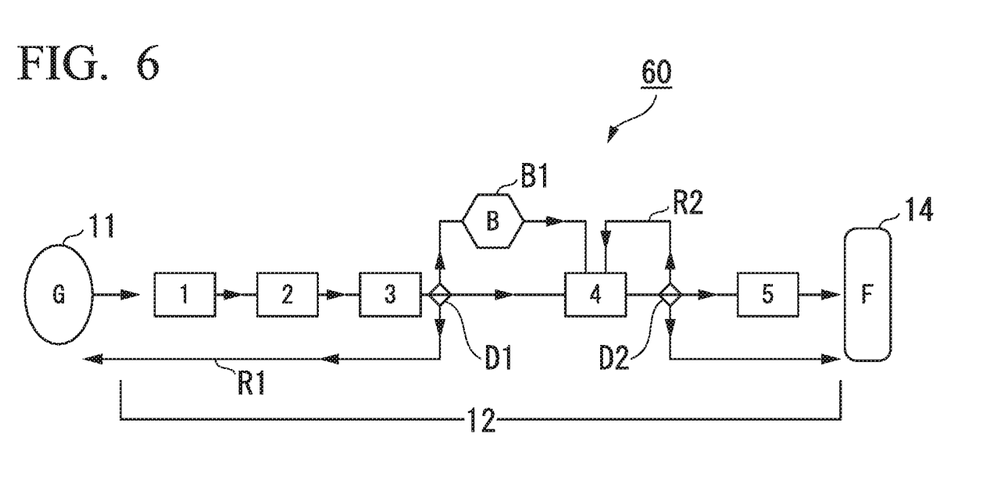
FIG. 6 is a schematic view of the organic substance production system 60 according to the sixth embodiment of the present invention.

As shown in FIG. 6, the organic substance production system 60 of the sixth embodiment of the present invention includes a synthesis gas generation furnace 11, a synthesis gas purification unit 12, and an organic substance synthesis unit 14. In this respect, the production system 60 is the same as the production systems 10, 20, 30, 40 and 50.

The synthesis gas purification unit 12 includes a first purification unit for purifying the synthesis gas generated in the synthesis gas generation furnace 11, a second purification unit for purifying the synthesis gas purified by the first purification unit, and a detection unit for measuring the impurity concentration in the synthesis gas purified by the first purification unit.

The detection unit feeds the synthesis gas purified in the first purification unit to the second purification unit when the impurity concentration is not higher than a predetermined value. On the other hand, when the impurity concentration is higher than the predetermined value, the detection unit returns the synthesis gas purified in the first purification unit to the first purification unit or the synthesis gas generation furnace.

The predetermined value of the impurity concentration can be set, for example, in view of the adverse effect on the microorganisms as described above.

The synthesis gas purification unit 12 includes a scrubber 1, a gas chiller 2, a desulfurization tank 3, a PSA 4, an activated carbon tank 5, a first detector D1, a second detector D2, a first return pipe R1, and a second return pipe R2, which are sequentially connected between the synthesis gas generation furnace 11 and the organic substance synthesis unit 14. These are connected via piping denoted by arrows in the drawing.

<Organic Substance Production Method 60>

A method 60 which can be mentioned as an example of embodiments in which an organic substance is produced using the organic substance production system 60 includes a step of generating the synthesis gas in the synthesis gas generation furnace 11, a step of purifying the synthesis gas in the synthesis gas purification unit 12, and a step of generating an organic substance from the purified synthesis gas in the organic substance synthesis unit 14.

In the synthesis gas purification step, first, a step of purifying the synthesis gas from the synthesis gas generation furnace 11 with the first purification unit to reduce the impurity concentration of the synthesis gas in the first purification unit, and a step of measuring the impurity concentration in the synthesis gas purified in the first purification unit by the detection unit (detection step) are performed.

When the impurity concentration measured in the detection step is not higher than a predetermined value, the synthesis gas purified in the first purification unit is fed to the second purification unit to further purify the synthesis gas. On the other hand, when the impurity concentration measured in the detection step is higher than the predetermined value, the synthesis gas purified in the first purification unit is returned to the first purification unit or the synthesis gas generation furnace.

The predetermined value of the impurity concentration can be set, for example, in view of the adverse effect on the microorganisms as described above.

A specific example of an embodiment in which an organic substance is produced using the organic substance production system 60 will be described below.

First, the synthesis gas from the synthesis gas generation furnace 11 is treated with the scrubber 1, the gas chiller 2 and the desulfurization tank 3, and then the concentration of impurities, such as $H_2S$, contained in the obtained synthesis gas is measured by the detector D1.

When the impurity concentration is not higher than the predetermined value, the synthesis gas is fed into the PSA 4, or the synthesis gas is fed into the first dilution tank B1.

When the impurity concentration is higher than the predetermined value, the synthesis gas is fed into the first dilution tank B1 and mixed with a synthesis gas having an impurity concentration not higher than the predetermined value, or the synthesis gas is returned to the synthesis gas generation furnace 11 via the first return pipe R1.

The predetermined value of the impurity concentration can be set, for example, in view of the adverse effect on the microorganisms as described above.

When the synthesis gas is fed into the first dilution tank B1, the synthesis gas having a high impurity concentration is diluted in the same manner as in the above-described production method 50, and the resulting synthesis gas with reduced impurity concentration is fed from the first dilution tank B1 to the PSA 4.

However, when the first detector D1 detects an impurity concentration exceeding the dilution capacity of the first dilution tank B1, the synthesis gas is returned to the synthesis gas generation furnace 11 via the first return pipe R1.

According to the above method, it is possible to prevent the highly concentrated impurities having passed through the desulfurization tank 3 from inflicting irreparable damage on the purification apparatus provided downstream.

In the method exemplified above, any one or more of the scrubber 1, the gas chiller 2 and the desulfurization tank 3 is the first purification unit, and the PSA 4 is the second purification unit.

Subsequently, as shown in FIG. 6, the concentration of various impurities contained in the synthesis gas from the PSA 4 is measured by the second detector D2.

When the impurity concentration is not higher than the predetermined value, the synthesis gas is fed into the activated carbon tank 5, or the synthesis gas is fed into the organic substance synthesis unit 14.

On the other hand, when the impurity concentration is higher than the predetermined value, the synthesis gas is returned to the PSA 4 via the second return pipe R2. Then, the returned synthesis gas is treated again in the PSA 4 to reduce the impurity concentration thereof, followed by measuring the impurity concentration in the synthesis gas again by the second detector D2. When the impurity concentration is not higher than the predetermined value, the synthesis gas is fed into the activated carbon tank 5 or the organic substance synthesis unit 14.

According to the above configuration, it is possible to prevent the highly concentrated impurities having passed through the PSA 4 from inflicting irreparable damage on the purification apparatus provided downstream. Further, unnecessary use of the activated carbon tank 5 can be avoided so as to prolong the service life of the activated carbon tank 5, which enables reduction of the running cost.

The predetermined value of the impurity concentration can be set, for example, in view of the adverse effect on the microorganisms as described above.

In the method exemplified above, any one or more of the scrubber 1, the gas chiller 2, the desulfurization tank 3, and the PSA 4 is the first purification unit, and the activated carbon tank 5 is the second purification unit.

Other Embodiments

The elements, combinations thereof, etc. that are explained above in connection with the specific embodiments of the present invention are mere examples, and various alterations such as addition of conventional element, omission and substitution of any elements, etc. may be made as long as such alterations do not deviate from the gist of the present invention.

For example, in the above-described production systems 30, 40, 50 and 60, at least one of TSA and PSA may be used in addition to the activated carbon tank 5, or the activated carbon tank 5 may be replaced by either one or both of TSA and PSA. In this instance, the number of TSA and PSA to be added or to replace may be one, or two or more. In addition, two or more activated carbon tanks 5 may be used. Further, if necessary, a gas treatment facility may be further provided on a downstream side of the system. For example, such a gas treatment facility may be a metal catalyst tank for removing oxygen or acetylene, a filter for preventing scattering of finely divided activated carbon, a pressure regulator, or the like.

EXAMPLES

Example 1

Using a production system which is the same as the production system 10 of FIG. 1, synthesis gas was produced and purified for producing ethanol.

The capacities of the first purification unit and the second purification unit were 90 L each. Activated carbon (type: 4 GS-S) manufactured by Tsurumicoal Co., Ltd. was filled into each of the first purification unit and the second purification unit.

The flow rate at which the synthesis gas obtained by partial oxidation of waste was fed to the first purification unit was 5 Nm$^3$/min.

A detector (microGC, "490 micro GC", manufactured by GL Science Co., Ltd.) for detecting the concentration of benzene was installed at the inlet (point A) of the first purification unit, the inlet (point B) of the first purification unit and the outlet (point C) of the second purification unit, and the concentration of benzene was constantly monitored. The detector installed at point B corresponds to the detector 12b of the production system 10 in FIG. 1. Referring to the measured value in the detector at point B, when the benzene concentration was not higher than the predetermined threshold value (20 ppm), the synthesis gas from the first purification unit was fed to the fermentor of the organic substance synthesis unit 14, and when the benzene concentration was higher than the threshold value (20 ppm), the synthesis gas from the first purification unit was fed to the second purification unit.

Table 1 below shows the benzene concentrations at points A, B and C at times 1 to 4. The blank cells in Table 1 indicate that the synthesis gas was not sent to point C.

TABLE 1

| Time | Benzene concentration (ppm) at point A | Benzene concentration (ppm) at point B | Benzene concentration (ppm) at point C |
|---|---|---|---|
| 1 | 1300 | 10 | |
| 2 | 4200 | 40 | Less than 5 |
| 3 | 1800 | 18 | |
| 4 | 6000 | 70 | 10 |

As shown in Table 1, at times 1 and 3 where the benzene concentration at point B was not higher than 20 ppm, the synthesis gas was fed from the first purification unit to the fermentor while bypassing the second purification unit. On the other hand, at times 2 and 4 where the benzene concentration at point B was higher than 20 ppm, the synthesis gas from the first purification unit was fed to the fermentor via the second purification unit.

As a result of operating the above production system for 4300 hours, the period of time during which the benzene concentration at point B exceeded 20 ppm as in times 2 and 4 was 280 hours. Accordingly, the period of time during which the second purification unit was used was 280 hours (about 6.5%) out of 4300 hours. Thus, in this case, deterioration of the activated carbon in the second purification unit was able to be suppressed more than the case of using the first and second purification units over the entire period of 4300 hours.

Example 2

Using a production system which is the same as the production system 30 of FIG. 1, synthesis gas was produced and purified for producing ethanol.

In the above production system, the PSA 4 was installed downstream of the desulfurization tank 3, and the activated carbon tank 5 was further provided downstream of the PSA 4. Further, at a position upstream of the desulfurization tank 3, a detector D1 for measuring the concentration of hydrogen sulfide, a flow path leading to the desulfurization tank 3, and a flow path directly connected to the PSA 4 while bypassing (skipping) the desulfurization tank 3 were provided.

The PSA 4 can accommodate therein various types of adsorbent/absorbent. The selection of appropriate adsorbent/absorbent and the application of pressure swing enabled adsorption/absorption of even a small amount of hydrogen sulfide. Therefore, even if several tens of ppm of hydrogen sulfide remains in the synthesis gas to be fed to the PSA 4, the synthesis gas can be treated with only the PSA 4 without using the desulfurization tank 3.

Using the above production system, the concentration of hydrogen sulfide contained in the synthesis gas was measured at the inlet of the desulfurization tank 3 by the detector D1, and only when a concentration exceeding 50 ppm (predetermined threshold value) was detected, the synthesis gas was fed to the desulfurization tank 3. On the other hand, when a concentration of not higher than 50 ppm was detected, the synthesis gas was sent to the PSA 4.

Comparative Example 2A

Using a production system which was the same as in Example 2 except that the production system was not provided with a flow path directly connected to the PSA 4 while bypassing the desulfurization tank 3 and a detector D1, synthesis gas was produced and purified for producing ethanol.

[Results of Evaluation]

In the production system of Example 2, the synthesis gas was not allowed to flow into the desulfurization tank 3 unless the hydrogen sulfide was contained at a high concentration in the synthesis gas; therefore, the period of time during which the gas was allowed to flow through the desulfurization tank 3 in Example 2 was short, as compared to that in Comparative Example 2A.

On the other hand, in the production system of Comparative Example 2A, the synthesis gas was allowed to constantly pass through the desulfurization tank 3, and the hydrogen sulfide was almost completely removed in the desulfurization tank 3. As a result, the service life of the desulfurization tank 3 in Comparative Example 2A was shortened to about ⅓ of that of the desulfurization tank 3 in Example 2.

DESCRIPTION OF THE REFERENCE SIGNS

10, 20, 30, 40, 50, 60: Production system
11: Synthesis gas generation furnace
12: Synthesis gas purification unit
12*a*: First purification unit
12*b*: Detection unit
12*c*: Second purification unit
14: Organic substance synthesis unit
15: Purifier
D1, D2: Detector
B1, B2: Dilution tank
R1, R2: Return pipe
1: Scrubber
2: Gas chiller
3: Desulfurization tank
4: Pressure swing adsorption apparatus (PSA)
5: Activated carbon tank

The invention claimed is:

1. A system for producing an organic substance, comprising:
a synthesis gas generation furnace for producing a synthesis gas by partially oxidizing a waste comprising a carbon source;
a synthesis gas purification unit which is connected to the synthesis gas generation furnace and purifies the synthesis gas generated in the synthesis gas generation furnace to reduce an impurity concentration in the synthesis gas; and
an organic substance synthesis unit which is connected to the synthesis gas purification unit and generates an organic substance from the synthesis gas purified in the synthesis gas purification unit,
wherein the synthesis gas purification unit comprises:
a first purification unit for purifying the synthesis gas;
a second purification unit for purifying the synthesis gas purified in the first purification unit, which has a higher ability to reduce an impurity concentration than the first purification unit; and
a detection unit for measuring an impurity concentration in the synthesis gas before being purified in the first purification unit and the second purification unit,
wherein the detection unit is configured to:
feed the synthesis gas to the first purification unit when the impurity concentration is not higher than a predetermined value, and
feed the synthesis gas to the second purification unit when the impurity concentration is higher than the predetermined value.

2. A system for producing an organic substance, comprising:
a synthesis gas generation furnace for producing a synthesis gas by partially oxidizing a waste comprising a carbon source;
a synthesis gas purification unit which is connected to the synthesis gas generation furnace and purifies the synthesis gas generated in the synthesis gas generation furnace to reduce an impurity concentration in the synthesis gas; and
an organic substance synthesis unit which is connected to the synthesis gas purification unit and generates an organic substance from the synthesis gas purified in the synthesis gas purification unit,
wherein the synthesis gas purification unit comprises:
a first purification unit for purifying the synthesis gas;
a second purification unit for purifying the synthesis gas purified in the first purification unit;
a mixing unit for sequentially receiving the synthesis gas from the first purification unit, mixing together a synthesis gas received earlier and a synthesis gas received later, and feeding resulting synthesis gas to the second purification unit; and
a detection unit for measuring an impurity concentration in the synthesis gas purified in the first purification unit,
wherein the detection unit is configured to:
feed the synthesis gas purified in the first purification unit to the second purification unit or the mixing unit when the impurity concentration is not higher than a predetermined value, and
feed the synthesis gas purified in the first purification unit to the mixing unit when the impurity concentration is higher than the predetermined value, to thereby mix the synthesis gas with a synthesis gas having an impurity concentration not higher than the predetermined value.

3. A system for producing an organic substance, comprising:
a synthesis gas generation furnace for producing a synthesis gas by partially oxidizing a waste comprising a carbon source;
a synthesis gas purification unit which is connected to the synthesis gas generation furnace and purifies the synthesis gas generated in the synthesis gas generation furnace to reduce an impurity concentration in the synthesis gas; and an organic substance synthesis unit which is connected to the synthesis gas purification unit and generates an organic substance from the synthesis gas purified in the synthesis gas purification unit, wherein the synthesis gas purification unit comprises:

a first purification unit for purifying the synthesis gas;

a second purification unit for purifying the synthesis gas purified in the first purification unit;

a detection unit for measuring an impurity concentration in the synthesis gas purified in the first purification unit, wherein the detection unit is configured to:

feed the synthesis gas purified in the first purification unit to the second purification unit when the impurity concentration is not higher than a predetermined value, and return the synthesis gas purified in the first purification unit to the first purification unit or the synthesis gas generation furnace when the impurity concentration is higher than the predetermined value.

4. The system according to claim 1, wherein the predetermined value of the impurity concentration is in a range of concentration that adversely affects anaerobic bacteria that produce the organic substance in the organic substance synthesis unit.

5. The system according to claim 1, wherein the first purification unit is a pressure swing adsorption apparatus or a temperature swing adsorption apparatus.

6. The system according to claim 1, wherein the second purification unit comprises activated carbon.

7. A method for producing an organic substance using the system according to claim 1, which comprises:

a step of generating a synthesis gas in the synthesis gas generation furnace;

a step of purifying the synthesis gas in the synthesis gas purification unit; and a step of generating an organic substance from the purified synthesis gas in the organic substance synthesis unit, wherein the step of purifying the synthesis gas comprises:

a step of measuring an impurity concentration in the synthesis gas by the detection unit; and a step of:

feeding the synthesis gas to the first purification unit when the impurity concentration is not higher than a predetermined value, thereby purifying the synthesis gas, or feeding the synthesis gas to the second purification unit when the impurity concentration is higher than the predetermined value, thereby purifying the synthesis gas.

8. A method for producing an organic substance using the system according to claim 2, which comprises:

a step of generating a synthesis gas in the synthesis gas generation furnace;

a step of purifying the synthesis gas in the synthesis gas purification unit; and a step of generating an organic substance from the purified synthesis gas in the organic substance synthesis unit, wherein the step of purifying the synthesis gas comprises:

a step of purifying the synthesis gas in the first purification unit;

a step of measuring an impurity concentration in the synthesis gas purified in the first purification unit by the detection unit; and a step of:

feeding the synthesis gas purified in the first purification unit to the second purification unit or the mixing unit when the impurity concentration is not higher than a predetermined value, or feeding the synthesis gas purified in the first purification unit to the mixing unit when the impurity concentration is higher than the predetermined value, to thereby mix the synthesis gas with a synthesis gas having an impurity concentration not higher than the predetermined value.

9. A method for producing an organic substance using the system according to claim 3, which comprises:

a step of generating a synthesis gas in the synthesis gas generation furnace;

a step of purifying the synthesis gas in the synthesis gas purification unit; and a step of generating an organic substance from the purified synthesis gas in the organic substance synthesis unit, wherein the step of purifying the synthesis gas comprises:

a step of purifying the synthesis gas in the first purification unit;

a step of measuring an impurity concentration in the synthesis gas purified in the first purification unit by the detection unit; and a step of:

feeding the synthesis gas purified in the first purification unit to the second purification unit when the impurity concentration is not higher than a predetermined value, or returning the synthesis gas purified in the first purification unit to the first purification unit or the synthesis gas generation furnace when the impurity concentration is higher than the predetermined value.

10. The method according to claim 7, wherein the predetermined value of the impurity concentration is in a range of concentration that adversely affects anaerobic bacteria that produce the organic substance in the organic substance synthesis unit.

* * * * *